(12) United States Patent
Schoess et al.

(10) Patent No.: US 11,141,100 B2
(45) Date of Patent: Oct. 12, 2021

(54) MOISTURE ASSESSMENT SYSTEM AND METHOD FOR WOUND CARE

(71) Applicant: Coloplast A/S, Humlebaek (DK)

(72) Inventors: Jeffrey N. Schoess, Howard Lake, MN (US); Matthew Allen Mueggenberg, Buffalo, MN (US); Christopher Alan Taylor, Buffalo, MN (US)

(73) Assignee: Coloplast A/S, Humlebaek (DK)

( * ) Notice: Subject to any disclaimer, the term of this patent is extended or adjusted under 35 U.S.C. 154(b) by 968 days.

(21) Appl. No.: 15/390,439

(22) Filed: Dec. 23, 2016

(65) Prior Publication Data

US 2019/0192066 A1 Jun. 27, 2019

Related U.S. Application Data

(60) Provisional application No. 62/387,300, filed on Dec. 23, 2015.

(51) Int. Cl.
*A61B 5/00* (2006.01)
*A61F 13/00* (2006.01)
*A61B 5/053* (2021.01)

(52) U.S. Cl.
CPC ............ *A61B 5/445* (2013.01); *A61B 5/0024* (2013.01); *A61B 5/053* (2013.01); *A61B 5/443* (2013.01);
(Continued)

(58) Field of Classification Search
CPC ......... A61B 5/00; A61B 5/053; A61B 5/6833; A61B 5/6801; A61B 5/443; A61B 5/447;
(Continued)

(56) References Cited

U.S. PATENT DOCUMENTS 6,433,244 B1 8/2002 Roe et al.
6,720,866 B1 * 4/2004 Sorrells ............. G06K 19/0717
340/10.34
(Continued)

FOREIGN PATENT DOCUMENTS

EP 3034054 A1 6/2016
KR 20170113930 A 10/2017
(Continued)

OTHER PUBLICATIONS

Mehmood N, Hariz A, Fitridge R, Voelcker NH. 2013. Applications of modern sensors and wireless technology in effective wound management. J Biomed Mater Res Part B 2013: 00B: 000-000.
(Continued)

*Primary Examiner* — Eric J Messersmith
(74) *Attorney, Agent, or Firm* — Coloplast Corp., Coloplast A/S; Nick Baumann

(57) ABSTRACT

A Wound Moisture and Assessment System includes a flexible coupon containing one or more electrochemical moisture sensors for measuring a moisture profile of a wound. The coupon is activated by a wireless RF scanner that provides power to the coupon for taking moisture measurements, receives the moisture measurements therefrom, and transmits the measurements to a computing device. The moisture measurements can be represented as a wound moisture map that allows a patient or caregiver to assess the health and healing progress of a wound such as an ulcer.

19 Claims, 9 Drawing Sheets

(52) U.S. Cl.
CPC ............ *A61B 5/447* (2013.01); *A61B 5/6801* (2013.01); *A61B 5/6813* (2013.01); *A61B 5/6833* (2013.01); *A61F 13/00017* (2013.01); *A61F 13/00038* (2013.01); *A61F 13/00055* (2013.01); *A61F 2013/00429* (2013.01); *A61F 2013/00442* (2013.01); *A61F 2013/00604* (2013.01); *A61F 2013/00944* (2013.01); *A61F 2013/00961* (2013.01)

(58) Field of Classification Search
CPC ..... A61B 5/6813; A61B 5/0024; A61B 5/445; A61F 13/00; A61F 13/00055; A61F 13/00038; A61F 13/00017; A61F 2013/00604; A61F 2013/00944; A61F 2013/00961; A61F 2013/00429; A61F 2013/00442
See application file for complete search history.

(56) References Cited

U.S. PATENT DOCUMENTS

| | | | |
|---|---|---|---|
| 6,774,800 B2* | 8/2004 | Friedman | A61B 5/0002 340/572.5 |
| 7,456,744 B2 | 11/2008 | Kuhns et al. | |
| 7,948,380 B2 | 5/2011 | Kuhns et al. | |
| 8,978,452 B2* | 3/2015 | Johnson | A61F 13/42 73/74 |
| 9,070,060 B2 | 6/2015 | Forster | |
| 9,506,886 B1* | 11/2016 | Woodbury | A61F 13/42 |
| 9,526,439 B2 | 12/2016 | Connelly et al. | |
| 9,649,230 B1* | 5/2017 | Li | A61F 13/42 |
| 10,022,277 B2* | 7/2018 | Heil | A61F 13/42 |
| 2008/0061965 A1* | 3/2008 | Kuhns | G06K 19/0672 340/539.22 |
| 2013/0271278 A1 | 10/2013 | Duesterhoft et al. | |
| 2013/0274563 A1 | 10/2013 | Duesterhoft et al. | |
| 2013/0274629 A1 | 10/2013 | Duesterhoft et al. | |
| 2014/0027295 A1* | 1/2014 | Chiao | G01N 27/403 205/122 |
| 2014/0200538 A1* | 7/2014 | Euliano | A61F 13/42 604/361 |
| 2014/0298928 A1* | 10/2014 | Duesterhoft | A61F 13/00051 73/865.8 |
| 2015/0018792 A1* | 1/2015 | Marsiquet | A61F 13/0246 604/361 |
| 2016/0166438 A1* | 6/2016 | Rovaniemi | A61F 13/00059 600/301 |
| 2016/0267769 A1* | 9/2016 | Rokhsaz | H01Q 9/04 |

FOREIGN PATENT DOCUMENTS

| | | |
|---|---|---|
| WO | WO2012054474 A1 | 4/2012 |
| WO | 2016166731 A1 | 10/2016 |

OTHER PUBLICATIONS

Mehmood, N., et al., A flexible and low power telemetric sensing and monitoring system for chronic wound diagnostics; Biomed Eng Online; 14:17; 2015.

* cited by examiner

MOISTURE ASSESSMENT SYSTEM AND METHOD FOR WOUND CARE

CROSS REFERENCE TO RELATED APPLICATIONS

This application claims priority to and the benefit under 35 USC § 119(e) of U.S. Provisional Patent Application No. 62/387,300, filed on Dec. 23, 2015, the contents of which are incorporated by reference in their entirety as if fully set forth herein.

STATEMENT REGARDING FEDERALLY SPONSORED RESEARCH OR DEVELOPMENT

Research and development of the concepts disclosed herein were funded in part by the National Institutes of Health, National Institute of Diabetes and Digestive and Kidney Diseases, Grant No. 5R44DK09787-04. The United States Government may have certain rights to the claimed invention.

TECHNICAL FIELD

This disclosure relates to systems and methods for monitoring wound moisture and exudate levels. The disclosed systems and methods can be used to guide the treatment of wounds by clinicians in a hospital or similar setting or by patients opting to self-manage their wounds.

BACKGROUND

Chronic wounds affect approximately 4 million people annually in the United States. With a growing elderly population, increasing incidence of diabetes, venous stasis ulcers, and pressure ulcers (PUs), along with rapidly rising wound care costs, wound care is a significant public health problem. It is estimated that at least 1.7 million people develop pressure ulcers annually, at a cost of $2.2 to $3.6 billon (Langemo, D K, The Lived Experience of Having a Pressure Ulcer: A Qualitative Analysis Adv Skin Wound-Care; 13:225-35; 2000). Venous stasis ulcers also present a major health management challenge for health care professionals. It is estimated that approximately 1% of the general population and 3.5% of persons over age 65 have venous stasis ulcers with numbers rising as the population ages (Hess, C. T., Management of the Patient with a Venous Ulcer, Adv Skin WoundCare; 13(2); March-April 2000; pp. 79-83). The recurrence rate of venous stasis ulcers is approaching 70% (Bryant R A, editor. Acute and Chronic Wounds. St Louis: Mosby; 1992 p. 164-204). The estimated per-episode cost of care can exceed $40,000 (Rudolph, D. M. Pathophysiology and Management of Venous Ulcers. J Wound Ostomy Continence Nurs 1998; 25: 248-55) with a total cost of treatment estimated to be $2.5 to $3.5 billion (Onegnae, K. Phillips, T. Leg Ulcer Management. Emerg Med 1993; 25:45-53).

The ability of a body to self-heal a wound is dependent, in part on its ability to maintain optimum moisture levels throughout and immediately surrounding the wound bed. Too little moisture can lead to dryness, cracking and irritation; too much moisture, e.g., chronic exudate overproduction, can lead to infection and tissue breakdown. In many cases, wounds are covered with protective dressings to generally protect the wound bed itself; however, this sometimes precludes the ability to monitor the state of the wound including, in particular, the moisture level. Removing a dressing to examine a wound can itself lead to irritation and disruption of the healing process, especially if the dressing is intended to protect the wound for extended periods of time.

SUMMARY

In one exemplary aspect, a coupon for wireless communication with a transceiver is provided. The coupon includes a flexible substrate having a top surface and a bottom surface, a radio-frequency antenna circuit disposed on the top surface of the flexible substrate, and at least one electrochemical moisture sensor circuit disposed on the bottom surface of the flexible substrate.

In one embodiment, the coupon further includes a near-field communications module disposed on the top surface of the flexible substrate that is in electronic communication with the radio-frequency antenna circuit. In a related embodiment, the near-field communications module includes a microcontroller in signal communication with the radio-frequency antenna circuit and the at least one electrochemical moisture sensor circuit, and a memory for storing executable logic functions for measuring a moisture value of an environment proximal to the at least one electrochemical moisture sensor circuit. In a further related embodiment, the near-field communications module further includes a multiplexer in signal communication with the microcontroller and the at least one electrochemical moisture sensor circuit, a signal converter capable of converting analog signals to digital signals and vice-versa, and an optional temperature sensor.

In one embodiment, the coupon further includes a bacteria sensor disposed on the bottom surface of the flexible substrate that is in signal communication with the near-field communications module.

In one embodiment, the near-field communications module is configured to receive operational power from an external radio-frequency source that is received by the radio-frequency antenna circuit.

In one exemplary aspect, a system for wirelessly obtaining a moisture measurement is disclosed. The system includes a wireless reader including a transceiver configured to emit and receive radio frequency signals and a coupon. The coupon includes a flexible substrate having a top surface and a bottom surface, at least one electrochemical moisture sensor circuit disposed on the bottom surface of the flexible substrate that is configured to determine a moisture value, an antenna circuit disposed on the top surface of the flexible substrate configured to at least receive the radio frequency signals from the transceiver, and a microcontroller in electronic communication with the antenna circuit and the at least one electrochemical moisture sensor circuit.

In one embodiment, the system further includes a bacteria sensor circuit disposed on the bottom surface of the flexible substrate and configured to be in electronic communication with the microcontroller.

In one embodiment, the microcontroller is configured to obtain the moisture value from the at least one electrochemical moisture sensor circuit. In a related embodiment, the microcontroller is configured to wirelessly transmit the moisture measurement to the wireless reader via the antenna circuit.

In one embodiment, the moisture value is determined by obtaining a capacitance value of the at least one electrochemical moisture sensor circuit.

In one embodiment, the coupon is disposed on, or within a wound dressing or bandage. In one embodiment, the microcontroller is configured to be powered by the radio frequency signal emitted by the transceiver of the wireless reader.

In one embodiment, the coupon includes an array of electrochemical moisture sensor circuits, each in signal communication with the microcontroller. In a related embodiment, the system further includes a multiplexer in electronic communication with the microcontroller that is configured for obtaining a capacitance value of each of the electrochemical moisture sensor circuits.

In one exemplary aspect, a system for generating a wound moisture map is disclosed. The system includes a flexible coupon having a top surface and a bottom surface, wherein the bottom surface is configured to be applied at least in part to a wound or ulcer. The system further includes an antenna circuit and a microcontroller disposed on the top surface of the coupon, wherein the microcontroller is in electronic communication with the antenna circuit, and a plurality of electrochemical moisture sensor circuits disposed on the bottom surface of the coupon. Each electrochemical moisture sensor circuit of the plurality of electrochemical moisture sensor circuits is in electronic communication with the microcontroller, and the antenna circuit is adapted to send and receive radio frequency signals to and from a remote radio frequency transceiver, respectively.

In one embodiment, the system further includes an electrochemical bacteria sensor disposed on the bottom surface of the coupon that is in electronic communication with the microcontroller.

In one embodiment, the system further includes an electronic temperature sensor disposed on the bottom surface that is in electronic communication with the microcontroller.

In one embodiment, the microcontroller is configured to receive query signals from the transceiver via the antenna, query the plurality of electrochemical moisture sensor circuits in a selective- or group-wide modality for one or more wound moisture measurements, and transmit the moisture measurements to the transceiver via the antenna.

In one embodiment, each electrochemical moisture sensor circuit of the plurality of electrochemical moisture sensor circuits includes an array of interdigitated electrodes.

Certain advantages of the systems and methods include: low cost fabrication polymer thick-film (screen-printing), disposability, body-worn comfort, lightweight construction (e.g., printing on a polymeric substrate), real-time measurement capability to aid clinical management of wounds, wireless communication, adaptability to several dressing types (e.g., transparent film, foam, composite), a noninvasive approach with the ability to assess moisture without dressing removal (thereby reducing risk to pathogens, decrease number of dressing changes and in turn strengthening new epidermal tissue), ability to map the pattern of moisture across the wound surface (e.g., measuring wound moisture distribution and time variation).

Further advantages include the ability to quantify moisture imbalance in wounds, the ability to administer timely and effective management of exudate levels, the ability to integrate wound moisture assessments into Electronic Medical Records systems for a variety of reasons, including specialty wound clinics for outcomes research, the ability to provide a reimbursement strategy for use of moisture measurement based on objective wireless evidence and integration of wound management in telecare or online decision support systems, especially for remote rural settings and managed care homes.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which.

DETAILED DESCRIPTION OF ILLUSTRATIVE EMBODIMENTS

Overview

In general, a Wound Moisture Assessment System (hereinafter 'WMAS') includes, inter alia, a flexible coupon configured to be placed on, over or about a wound such as, but not limited to, an ulcer. The coupon includes, inter alia, one or more moisture sensors configured to measure moisture in contact with, or in the immediate vicinity of the moisture sensor. The coupon includes requisite electronic circuitry to communicate with a WMAS wireless reader (hereinafter 'reader'). The reader is configured to energize the coupon and receive measurements from the one or more moisture sensors. Moisture measurements can be analyzed using an analysis module integral with the reader, or, alternatively, moisture measurements can be transmitted to a computing system where analysis of wound moisture data can be processed for visualization, storage, integration with medical health records, transmission to a remote caregiver, or other functions. In a preferred embodiment, data transfer between the reader and coupon, and energization of the coupon by the reader occurs wirelessly. In general, the coupon can be configured with a desired number and type of moisture sensor(s), and a desired modality supporting wireless interrogation of the coupon by the reader.

By integrating a plurality of moisture sensors into the coupon, a moisture 'map' of a wound bed can be obtained. These data can then be used by, for example, the patient or a caregiver to monitor the healing process of the wound or to alert the patient or caregiver of a critical moisture imbalance that may delay or preclude healing or indicate infection.

Figure 1:
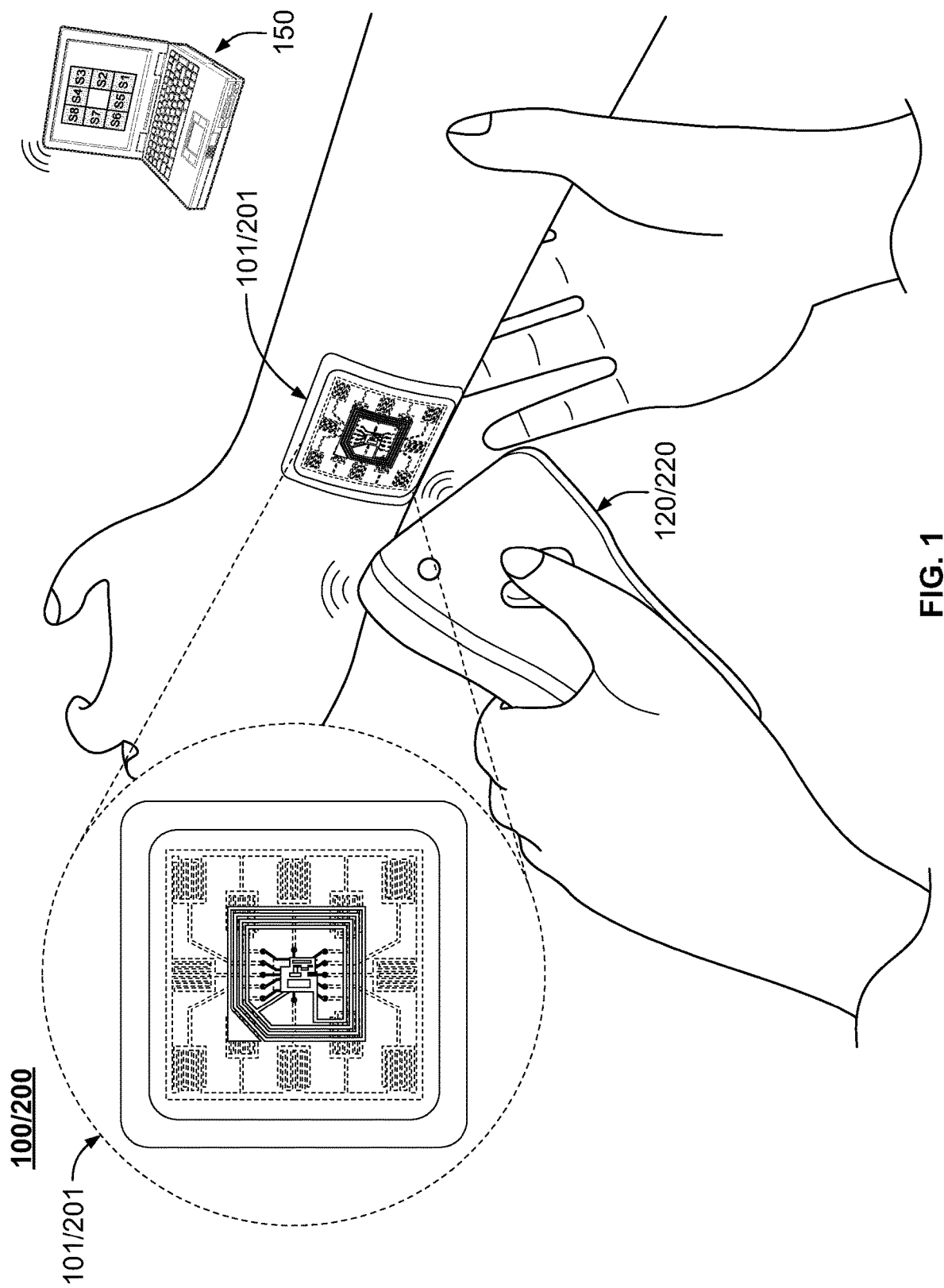
FIG. 1 illustrates a wound moisture assessment system (WMAS) according to one embodiment.

For example, referring to FIG. 1, WMAS 100/200 (and use thereof) is illustrated according to one embodiment. As discussed in greater detail below, a WMAS can utilize an analog or digital moisture sensor data collection schema, which are discussed herein as WMAS 100 and WMAS 200, respectively. Although coupon 201 is illustrated, FIG. 1 refers to coupon 101/201 and reader 120/220 to illustrate that, in a general sense, those elements are used in the same way by a patient, caregiver, doctor or other user. In this embodiment, the WMAS 100 includes a flexible coupon 101 that itself includes an array of moisture sensors.

In this embodiment, the coupon 101 is configured to be applied over a wound, e.g., directly, in cooperation with an adhesive, or the coupon 101 can be integrated with a wound dressing as described in greater detail herein. The coupon 101 is configured for wireless communication with a wireless reader 120. The coupon 101 can be interrogated (i.e., moisture sensor readings can be obtained), by positioning the wireless reader 120 within range of the coupon 101 which triggers data collection of the moisture sensor(s). A single reading can provide real-time quantification of wound bed etiology; multiple sensor readings can be assembled into a moisture map to monitor wound healing over time or to identify that a wound is worsening or becoming infected, for example. Because interrogation of the coupon 101 is wireless, wound moisture and exudate levels can be determined without removing the protective coupon or dressing from the wound, which is one advantage of the WMAS 100 over traditional bandages and wound dressings.

Interrogation of the coupon 101 by reader 120 can be accomplished by at least two approaches, each of which is described separately below. The first approach uses an analog radio frequency (RF) coupling between reader and coupon, and the second approach uses a digital schema. In both cases, the reader can communicate with a computing device 150.

Computing device 150 can be, without limitation, a personal computer, workstation, personal data assistant, cellular telephone, tablet or other electronic device that is capable of sending and receiving data signals and at least displaying wound moisture data as generally described herein. Computing device 150 can also communicate with reader 120 directly, or by known networking communications protocols, e.g., TCP, UDP, ICMP, HTTP, etc., through local (e.g., LAN), wide-area (e.g., WAN) networks, including the Internet, which can be accomplished by wired or wireless connections, e.g., Ethernet, LTE, WIFI, Bluetooth®, IR, WirelessHD, WiGig, etc., without limitation. Computing device 150 can be used, e.g., to display and store data collected by reader 120 in a user-friendly format, such as to display moisture maps as described herein.

Reader/Coupon Wireless Coupling: Analog Schema

Figure 2:
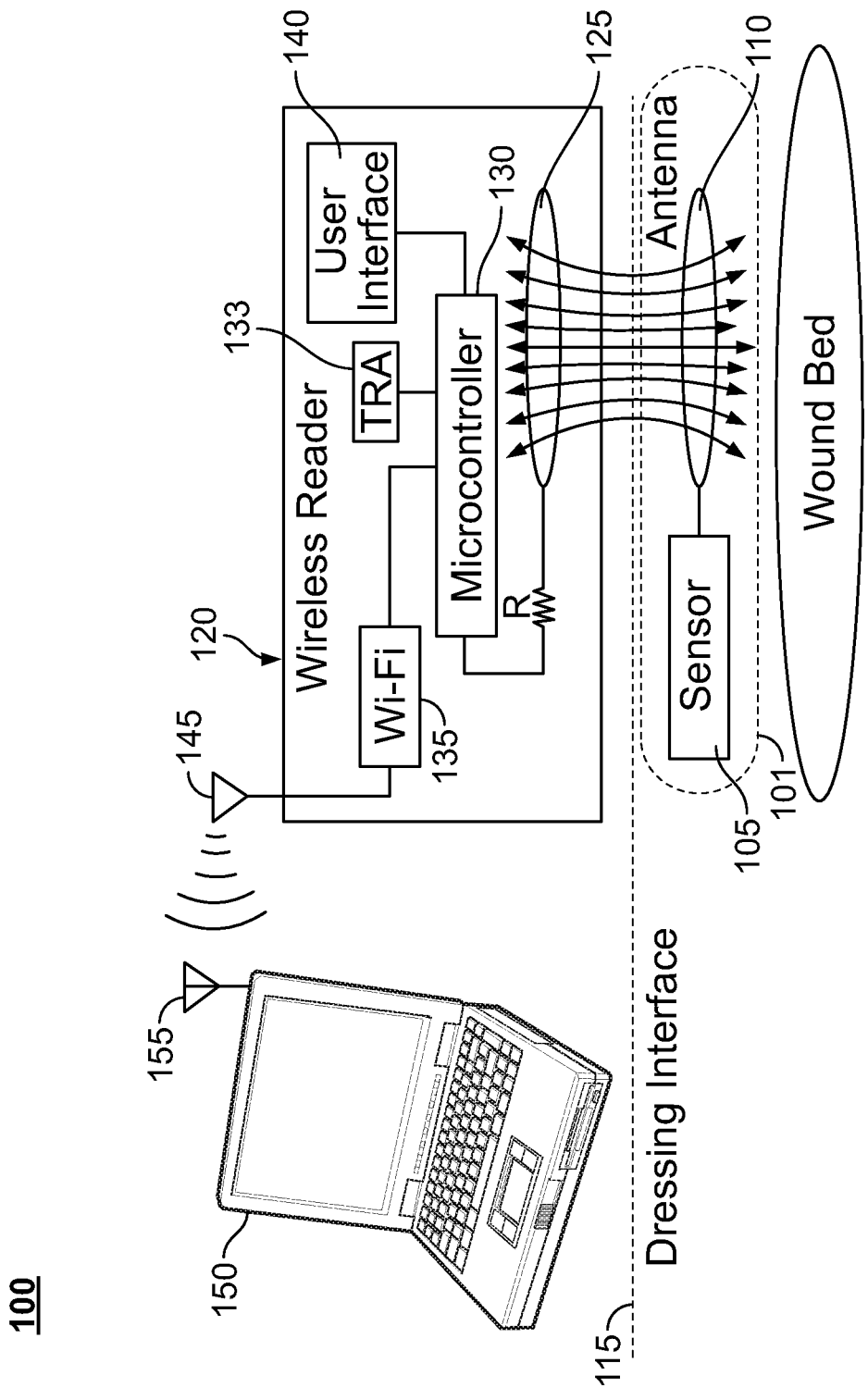
FIG. 2 is a functional diagram of a WMAS according to one embodiment.

Referring now to FIG. 2, a functional illustration of a WMAS 100 is shown according to one embodiment. In this embodiment, wireless coupling between the reader and coupon is accomplished using an analog schema. In the description that follows, the electronic circuit components of the coupon 101 can be disposed on coupon 101 by desired methods. However, a preferred method is ink-jet circuit deposition using a bio-friendly conductive ink such as silver nanoparticle ink.

Figure 3:
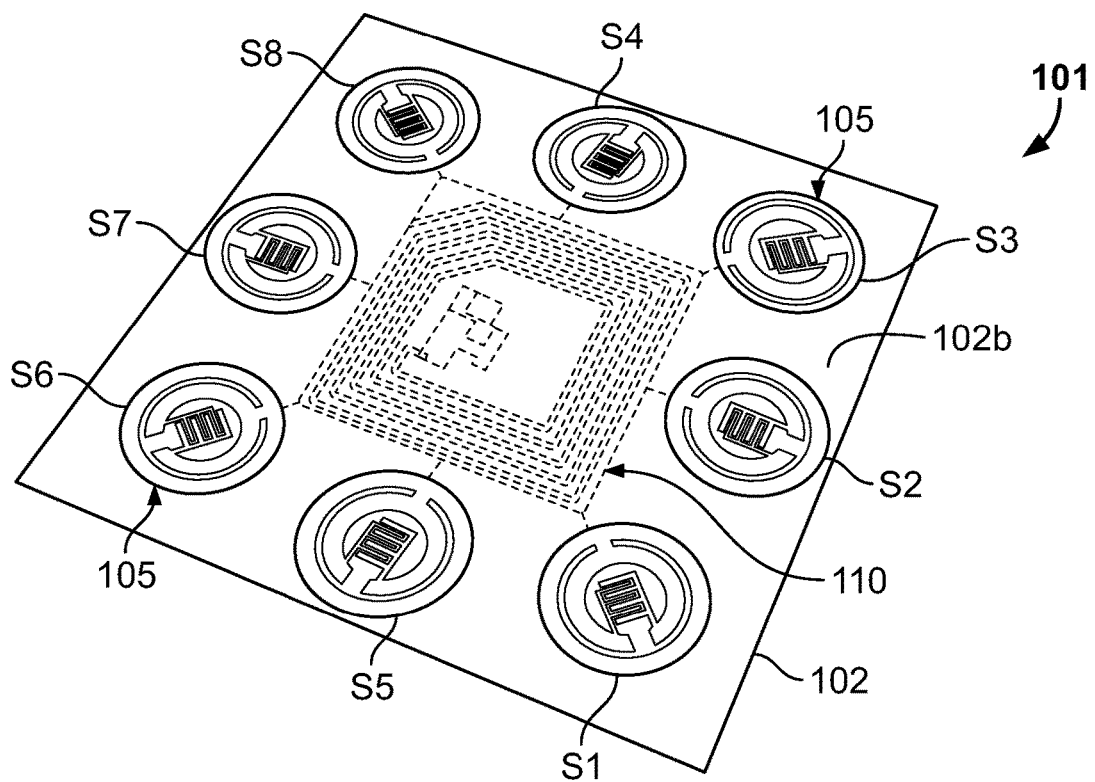
FIG. 3 illustrates a WMAS coupon according to one embodiment.

Referring to FIGS. 2-3, in this embodiment, the coupon 101 includes a flexible substrate 102 such a thin film of boPET (biaxially-oriented polyethylene terephthalate) having a top side (surface) 102a and a bottom side (surface) 102b. An antenna circuit (hereinafter 'antenna') 110 is disposed on the top side 102a of the substrate and is configured for receiving radio frequency (RF) energy from a transceiver 125 of reader 120. In this embodiment, at least one moisture sensor circuit 105 is disposed on the bottom side 102b of the substrate. In this embodiment, each moisture sensor 105 is in electronic signal communication with coupon antenna 110.

In this embodiment, antenna 110 is one which can be activated by proximity-based inductive coupling with transceiver 125, which provides a RF emission source. In general, the wireless reader 120 and the coupon 101 can communicate in a similar fashion as passive RFID systems. Each moisture sensor 105 is in electronic communication with the antenna 110; e.g., they can be connected by a stenciled circuit path. This configuration allows RF energy received by the antenna 110 to be delivered to the at least one moisture sensor 105 for the purpose of obtaining a moisture value from each moisture sensor as described in greater detail herein. Such an approach advantageously eliminates the need for a separate moisture sensor power source, such as a battery or wired connection to the coupon 101, providing the subject with the same type of unrestricted mobility as if he were wearing a regular wound dressing. Similarly, this configuration allows a coupon 101 to be placed on a wound for an extended period without needing to disturb the coupon to change batteries. This can reduce the likelihood of infection and minimize disturbance to the wound bed itself.

In this embodiment, transceiver 125 is configured to emit a controllable activation signal, e.g., an RF signal that is sufficient to power the at least one moisture sensor 105 when a moisture sensor reading is desired. In a preferred embodiment, antenna 110 is configured to receive the RF activation signal from transceiver 125 with minimal energy loss and shunt the energy to the at least one moisture sensor 105. In this embodiment, each of the one or more moisture sensors 105 can be used to collect a moisture sensor reading, e.g., a moisture value, or other value that can be converted or interpreted as a moisture level, which can be communicated back to transceiver 125 via antenna 110 as described in greater detail herein.

In coupon embodiments where multiple moisture sensors are used, each moisture sensor 105 can optionally have a separate, dedicated antenna operably associated with it. In such an embodiment, each dedicated antenna can encompass the associated moisture sensor so that each moisture sensor/antenna pair can be interrogated individually by the reader 120. In a preferred approach, a programmable microcontroller 130 (discussed below) can be configured to activate and collect a moisture reading from each moisture sensor 105 individually, e.g., in a round-robin fashion.

Alternatively, in a different embodiment, a single antenna can energize an array of moisture sensor circuits, wherein each moisture sensor circuit of the array can be configured with a unique conductance and capacitance to provide a uniquely-identifiable sensor impedance range. In such an approach, the backscattered resonant waveform can then include several resonant peaks, e.g., a unique peak frequency for each moisture sensor circuit, wherein each moisture sensor circuit can be present in a specific frequency band. The frequency band can be dependent on the characteristic impedance of each moisture sensor circuit.

In this embodiment, the reader 120 includes a programmable microcontroller 130 in electronic signal communication with the transceiver 125, a communications module 135 and a user interface module 140. In a preferred embodiment, microcontroller 130 includes at least a processor, a memory, and electronic data and command storage capabilities, e.g., RAM, ROM, a disk drive, cache, or other module for electronically storing instructions for activating the one or more moisture sensors 105 and receiving moisture sensor readings therefrom, preferably analyzing those data, and transmitting the moisture sensor reading results to a remote computing device.

In this embodiment, microcontroller 130 is in signal communication, e.g., through the use of an input/output port with user interface 140. User interface 140 can include, without limitation, a screen for displaying information relating to the acquisition of moisture sensor data, moisture analysis results and related data, historical data, and other information. In a preferred embodiment, user interface 140 can include a touch-sensitive display screen that provides the capability of entering user input, e.g., patient-identifying information, general system settings (date, time, interrogation frequency, etc.), computer network settings providing the capability of transmitting data from the WMAS 100 to a computer network, e.g., through the use of wired or wireless signal communications, activation buttons configured to initiate a wound moisture assessment, and other functions.

In this embodiment, microcontroller 130 is in signal communication with a communications module 135 that is configured to transmit moisture sensor readings to a remote computing device 150. The communications module 135 can be configured to provide bi-directional signal communication between the reader 120 and the remote computing device 150 by any preferred wired or wireless communications protocol or standard, such as WIFI, BLUETOOTH, IR, etc. In this embodiment, for wireless signal transmission, the communications module 135 communicates with remote computing device 150 using wireless antennas 145 and 155, respectively. In one embodiment, the wireless reader can be in the form of an RFID scanner gun which is configured to collect moisture sensor readings and transmit those data to computing device 150 for processing into a user-friendly format such as wound moisture map. In another embodiment which can also be applicable to WMAS 200, the reader can be integral with a smartphone or other personal communications device equipped with near-field scanning capabilities. In such an embodiment, the smartphone can include a software interface for activating scanning functionality and sending, storing and displaying data associated with a moisture sensor scan.

In this embodiment, to interrogate coupon 101 for the purpose of receiving a wound moisture assessment, the microcontroller 130 is configured in part to cause transceiver 125 to emit a pulse-width modulated (PWM) activation signal which can either directly drive the antenna 110, or, alternatively, the activation signal can be fed through an adjustable low-pass filter to supply a sine wave (SW) signal to the antenna 110. In this embodiment, either the PWM or SW signal is configured to generate an electromagnetic field coupling between the antenna 110 of the coupon 101 and the transceiver 125 of the wireless reader 120. In this embodiment, the microcontroller can generate a regulated alternating-current (AC) voltage signal that is applied to the transceiver 125 while simultaneously measuring the corresponding impedance of the at least one moisture sensor tag 105, as AC frequency f is varied. In this way, in this embodiment, moisture sensor readings are communicated from the coupon 101 to the reader 120.

Figure 4:
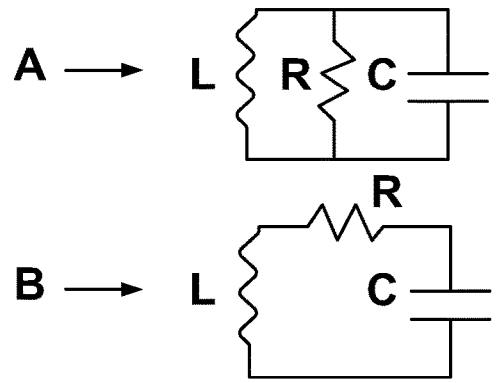
FIG. 4 illustrates a moisture sensor circuit according to one embodiment.

Referring to FIG. 4, a moisture sensor circuit e.g., of moisture sensor 105 is illustrated according to one embodiment. In this embodiment, moisture sensor 105 includes in part a resistor R, inductor (coil antenna) L, and capacitor C in a parallel (FIG. 4, A) or series (FIG. 4, B) resonant circuit configuration, also known as an RLC circuit as described in greater detail below. In this and other embodiments, the capacitor element of the RLC moisture sensor circuit can operate as an electrochemical transducer to measure or determine wound moisture.

Figure 5:
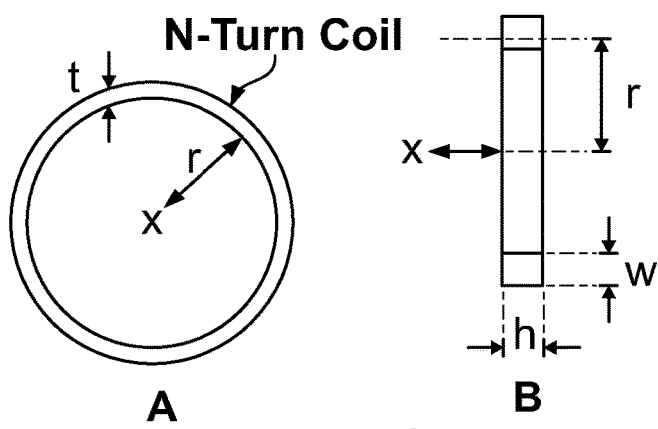
FIG. 5 illustrates a circular loop air coil antenna according to one embodiment.

Referring to FIG. 5, an exemplary circular loop air coil antenna, such as antenna 110 of reader 120, is shown in top (A) and side (B) views. The coil antenna can be a multi-layer coil antenna to form an inductance coil in limited space for wirelessly interrogating the one or more moisture sensors 105 of coupon 101. The at least one sensor 105 can be wirelessly interrogated by an electromagnetic field whose parameters depend at least in part on the physical design of the antenna, namely: an electric current I passing through the antenna coil, the antenna average radius r, the number of turns N in the antenna coil, the read-distance x along the central axis of the coil, the coil winding thickness t and coil winding height h. In this embodiment, the electromagnetic field created by antenna 110 induces a current and a potential drop in the at least one moisture sensor 105 of coupon 101.

In this embodiment, the antenna coil includes N turns, where r is the average radius of the coil, t is the winding thickness and h is the winding height. Using the inductance formula:

$$L = \frac{0.31(rN)^2}{6r + 9h + 10t}$$

with N=200, r=1.0 inch, h=0.05 cm (19.68 mils) and t=0.5 cm as preferred values according to one embodiment, a value of L=3.87 mH is obtained. To form a resonant circuit for 125 kHz RF operation, a resonant capacitor value can be calculated by the expression:

$$C = \frac{1}{(2\pi f)^2 L}$$

where f is the frequency (125 kHz) and L is 3.87 mH; a resonant capacitance value of 419 pF is thus computed in this exemplary embodiment.

Figure 6:
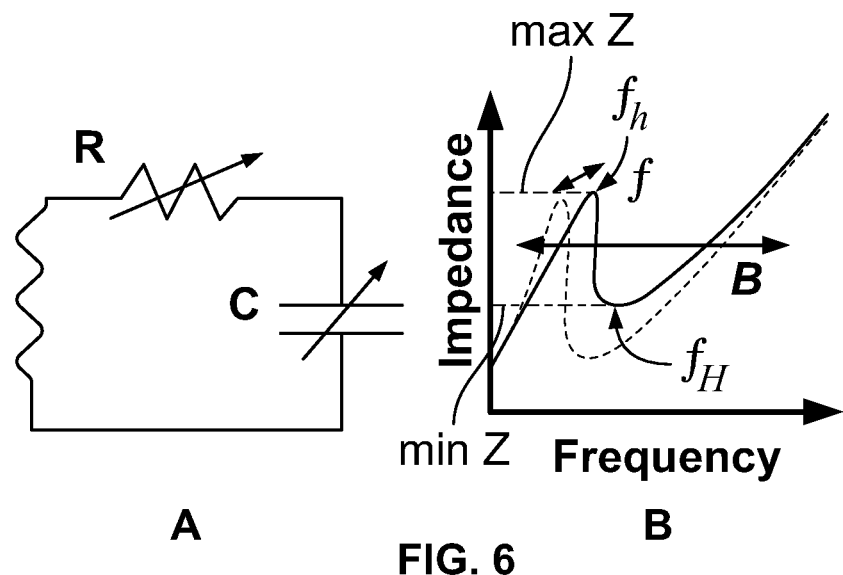
FIG. 6 illustrates frequency and bandwidth parameters of a moisture sensor circuit.

Referring now to FIG. 6, in general, each moisture sensor circuit can possess a characteristic (or resonant) frequency f and bandwidth B. Without wishing to be bound by theory, it has been discovered that the bandwidth, resonant frequency, and complex impedance Z of the RLC circuit of sensor 105 (FIG. 6A) is dependent upon a capacitance value, which itself is dependent upon a moisture level of the environment surrounding the at least one sensor 105. Thus, referring to FIG. 6B, a change in the moisture level of the surrounding environment can cause a corresponding, measurable shift and damping of the resonant frequency of the RLC resonator.

Still referring to FIG. 6B, in this example, the solid line shows sensor resonant impedance as a function of frequency. The bandwidth B of the sensor 105 circuit can be defined as the range between the peak of the maximum and minimum resonant values. The point corresponding to the lower frequency at half-power is $f_L$ and referred to as the lower cut-off frequency with the point corresponding to the upper cut-off frequency as $f_H$. The range between $f_H$ and $f_L$ can represent the bandwidth B as illustrated. The dashed line illustrates a shift and damping of the resonant impedance as a function of frequency (i.e., bandwidth) for a sensor 105 in a moist environment, where the complex impedance Z is given by the range between minimum and maximum values. Such a shift can be detected and analyzed, e.g., by microcontroller 130 of reader 120 as an impedance reflected in the antenna 110. This phenomenon can be exploited for qualifying and quantifying moisture levels of a wound bed when the sensor 105 is placed on or adjacent thereto.

Figure 7:
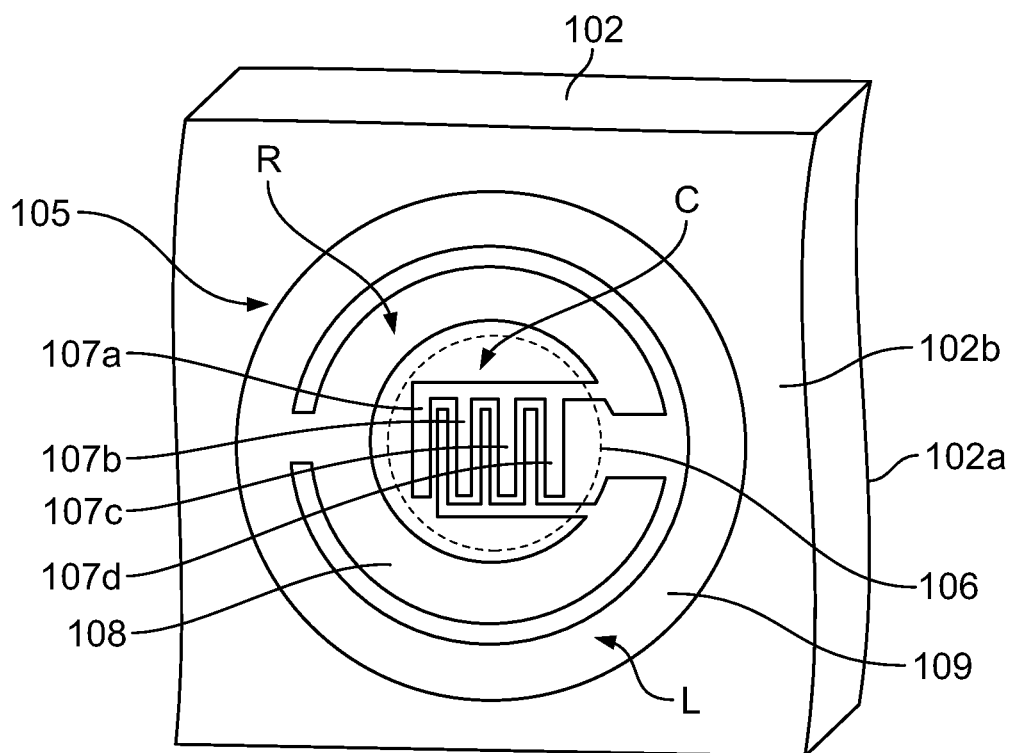
FIG. 7 illustrates a sensor circuit according to one embodiment.
Figure 8A:
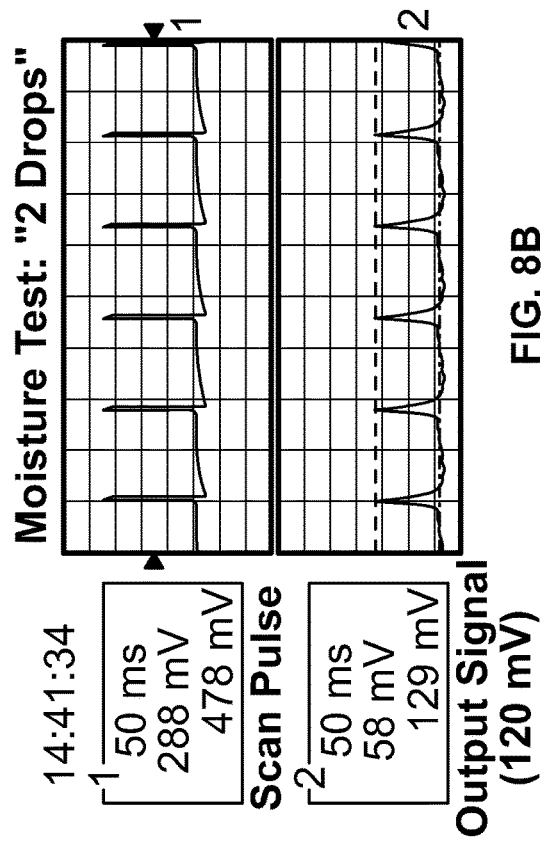
FIGS. 8A-8D show moisture test pulse and reflected waveforms, according to one embodiment of a WMAS.
Figure 8B:
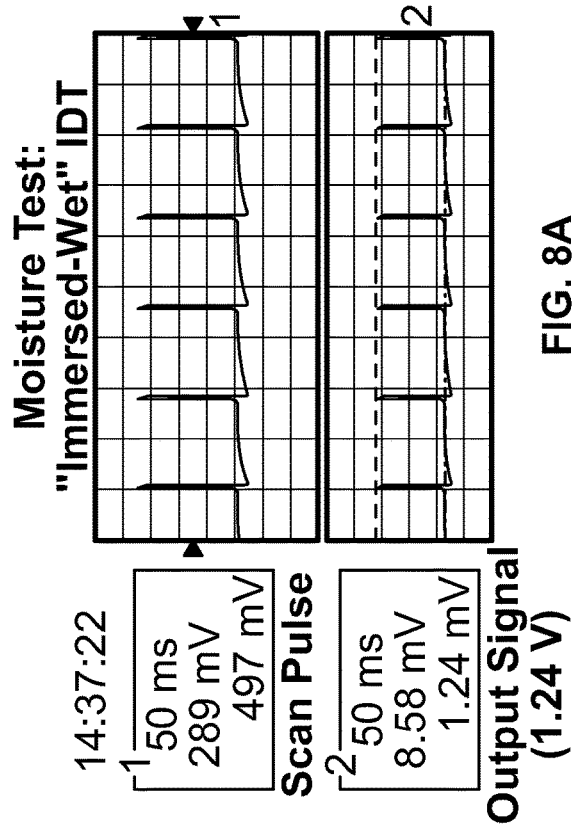
Figure 8C:
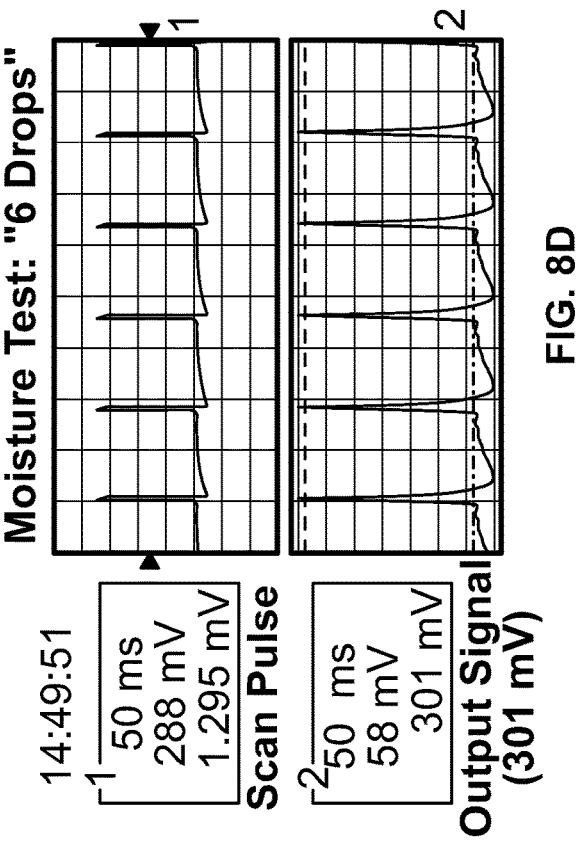
Figure 8D:
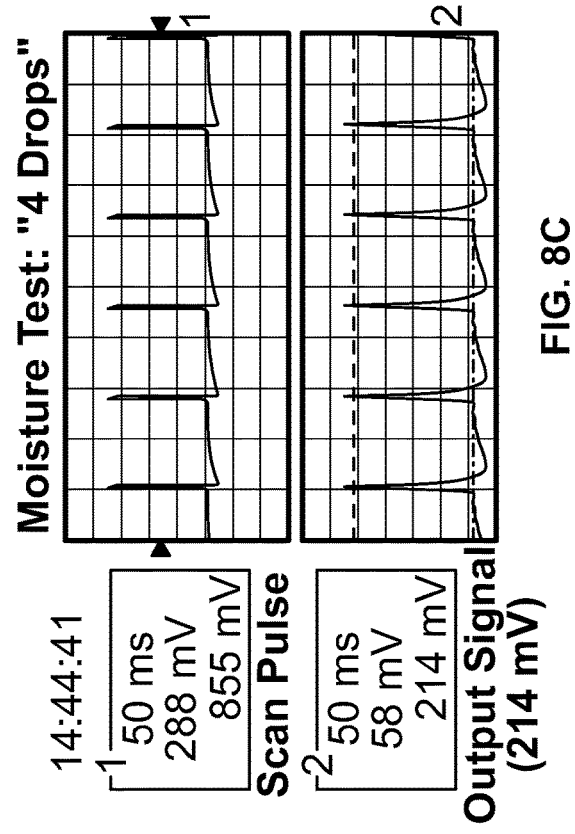

Referring now to FIG. 7, in this embodiment, each moisture sensor 105 is configured as an RLC resonator circuit. In this embodiment, the moisture sensor 105 includes a four-element electrode array (electrodes 107a-d) that together form a moisture transducer 106 and which acts as the capacitor in the RLC circuit. In this embodiment, each electrode (e.g., each of electrodes 107a-d) has a height dimension of about ⅛-inch, a width dimension of about ¹⁄₁₆-inch and the electrode-to-electrode spacing is about ¹⁄₃₂-inch. While the electrode dimensions disclosed here are suitable to enable the instant embodiment, it should be understood that other electrode dimensions and configurations can be substituted according to preference or to achieve operational characteristics as desired.

In this embodiment, the RLC circuit of the moisture sensor 105 further includes a substantially C-shaped resistor element 108 and a substantially ring-shaped inductor element 109 that surrounds both the C-shaped resistor element 108 and moisture transducer 106 as illustrated. Such a circuit can be printed, e.g., on a polyester film having about a five millimeter thickness with silver conductive polymer ink such that the moisture transducer 106, resistor 108 and inductor element 109 have thicknesses of about 1 mm. Exemplary printable conductors suitable for use in this capacity are DuPont's 5007 or 5025 printable silver conductors sold by DuPont, Research Triangle Park, N.C., USA; screen-printable silver ink nos. 1210 and 6105 provided by Methode (Chicago, Ill., USA); and product no. ECI 1005 provided by Henkel Electrical Materials, Irvine, Calif., USA.

Referring back to FIG. 3, in this and other embodiments, coupon 101 can include a plurality of moisture sensors 105 arranged as desired to achieve a preferred moisture sensor density across coupon 101. In FIG. 3, each individual moisture sensor is labeled S1-S8 to correspond with the discussion of moisture mapping that follows. In the exemplary illustration shown in FIG. 3, a plurality of moisture sensors 105 are in electronic communication with (i.e., through circuit connections), the centrally-disposed antenna 110 as shown. In this embodiment, each moisture sensor 105 of the coupon 101 can be configured to be individually readable by reader 120 for collecting wound moisture and exudate levels in an area adjacent to, or in contact with each individual sensor 105.

To achieve individual moisture sensor readings, in one embodiment, each sensor 105 can be configured to have a unique, identifiable resonant impedance profile, e.g., a resonance pattern through control of each printed sensor circuit. In such an embodiment, each resonant impedance profile can be measured for each sensor of the plurality of sensors and correlatively stored in memory. Each sensor can be identified by, e.g., one or more of a unique resonant impedance waveform shape (e.g., the solid line illustrated in FIG. 6B), unique positions or values of inflection points of the resonant impedance waveform, the amplitudes of selected resonant impedance waveform attributes, or a shift along the frequency axis—e.g., a change in bandwidth—of the impedance waveform. In general, the resonant impedance waveform can be measured for each individual sensor and correlatively stored with a particular sensor, e.g., sensor S1, sensor S2, etc. In one embodiment, each sensor 105 disposed on coupon 101 can be individually interrogated for a surrounding moisture level reading by modifying the transceiver output to match the characteristic resonant frequency of any selected sensor 105. In one embodiment, microcontroller 130 can be configured to make such output modifications in a step-wise order to interrogate each sensor present on a coupon 101.

In this and other embodiments, practices used in the RFID industry for minimizing signal collisions between tags can be applied to coupons having a plurality of sensors. For example, a WMAS 100 can be configured as a 'slotted Aloha' system where the activation of each sensor is delayed in a particular order, e.g., clockwise beginning with a sensor at the 12 o'clock position. In another approach, the WMAS 100 can be configured to utilize a so-called 'adaptive binary tree' protocol, where each sensor 105 is configured with a pre-programmed ID bit and is activated only when the wireless reader 120 transmits an initialization symbol and a matching bit ID or ID sequence. In yet another approach, an integrated circuit can be disposed on the coupon 101 and configured such that activation energy transmitted by the reader 120 and received by antenna 110 is shunted to each sensor S1-S8 in a particular order. For example, the integrated circuit can be configured to intercept the activation energy received by antenna 110, then shunt the activation energy to a first sensor S1, followed by a second, different sensor S2, and so on, until all sensors S1-S8 have been activated in a selected order. Each sensor reading can then be collectively used to create a moisture map.

Still referring to FIG. 3, in this embodiment, coupon 101 includes eight moisture sensors 105, labeled S1-S8; however, it should be understood that more or fewer moisture sensors can be used as preferred. The array of moisture sensors can be used for creating a map of wound moisture or exudate. In a preferred approach, such a map can be collected at selected intervals over a time period to monitor and manage acute and chronic wounds.

Referring now to FIG. 8, in this and other embodiments, determination of moisture or exudate levels and content from each moisture sensor can be accomplished, for example, using pulse symmetry analysis, alone or in combination with other analytical approaches. As described above, in this embodiment, moisture sensor 105 readings of coupon 101 can be obtained when reader 120 is activated to emit a PWM signal. The PWM signal can be received by antenna 110, and thereby generate an electromagnetic field coupling between the transceiver 125 and antenna 110 of the coupon 101. Microcontroller 130 can be configured to generate a regulated AC voltage signal that is applied to the transceiver 125 and, simultaneously, measure the corresponding impedance of the at least one coupon sensor 105 as AC frequency is varied. The resulting waveform, which correlates impedance as a function of AC frequency (hereinafter referred to as an "I/F waveform"), includes at least three features from which a moisture determination can be made: 1) the overall shape of the I/F waveform; 2) the amplitude of the I/F waveform; and 3) the symmetry of the I/F waveform pulse, which in this approach reflects the balance between leading and falling edges of the I/F waveform.

Without wishing to be bound by theory, it has been discovered that the amplitude, or overall height of the I/F waveform, e.g., relative to zero amplitude, can be used to reliably indicate the amount of moisture present in the vicinity of a sensor 105, and wet/dry cycling. The shape and symmetry of a I/F waveform can furthermore provide detailed information on the properties and chemistry of the fluid environment, such as electrochemical impedance, pH level and chemical composition (e.g., electrolyte identification), among other information.

In this embodiment, the reader 120 can be configured to power and communicate with the coupon 101 using a time pulse method. In this method, the reader 120 initiates a scan to read coupon 101 moisture by generating a time series pulse of known amplitude, width, and duty cycle. The antenna 110 captures the RF pulse wave transmitted from the reader 120 and the reflected impedance of the moisture sensor 105 is then analyzed by a time response analyzer (TRA) module 133 in the reader 120. The TRA module 133 can be an electronic circuit module configured to quantify the pulse symmetry of the reflected I/F waveform from the sensor 105, for example: 1) the overall shape of the I/F waveform, 2) the amplitude of the I/F waveform, and 3) the symmetry of the I/F pulse, which, in this approach can represent a balance between the leading and falling edges of the reflected I/F waveform.

For example, FIG. 8 shows scan pulse and reflected I/F waveforms (charts A-D) of WMAS 100 test data for a coupon 101 exposed to varying degrees of moisture. In this example, each set shows the reader 120 scan pulse waveform in the top chart, e.g., chart A1 and the reflected, or output signal I/F waveform from a sensor 105 in the bottom chart, e.g., in chart A2. Referring to chart A, in this example, a coupon 101 was immersed in a tap water solution to represent a soaked wound bandage. As compared to the scan pulse A1, in this example, the reflected I/F waveform A2 has a decreased amplitude but its bandwidth is substantially narrow, similar in magnitude to the scan pulse A1.

Referring to chart B of FIG. 8, in this example, the coupon was exposed to a damp environment by applying two drops ($1.7 \times 10^{-3}$ fluid ounces per drop) of tap water solution to a coupon 101. The resulting output I/F waveform B2 is broadened, e.g., measured at its full-width-half-maximum (FWHM) and shows a decreased amplitude compared to the scan pulse B1. Charts C and D show the effect of the I/F waveform shape, e.g., amplitude and width at FWHM showing a progressive shift toward greater output signal amplitude with increasing dampness and, concurrently, a greater negative deviation or 'recovery' following the excitation pulse with increasing sensor dampness.

In one embodiment, a correlative look-up table or a predictive mathematical model can be constructed from standard samples such as those shown in the charts of FIG. 8, so that dampness and other factors of a wound bandage can be accurately determined by the WMAS 100. For example, as FIG. 8 illustrates, and without wishing to be bound by theory, the amplitude of an I/F waveform appears to be dependent at least in part on the degree of dampness of the coupon 101 (and sensor 105 environment). Thus, the shape of the I/F waveform in general, e.g., amplitude, inflection and deflection points and areas, pulse width and other factors can be used to qualify and quantify exudate levels on or near a wound bed as described herein.

Reader/Coupon Wireless Coupling: Digital Schema

Figure 9:
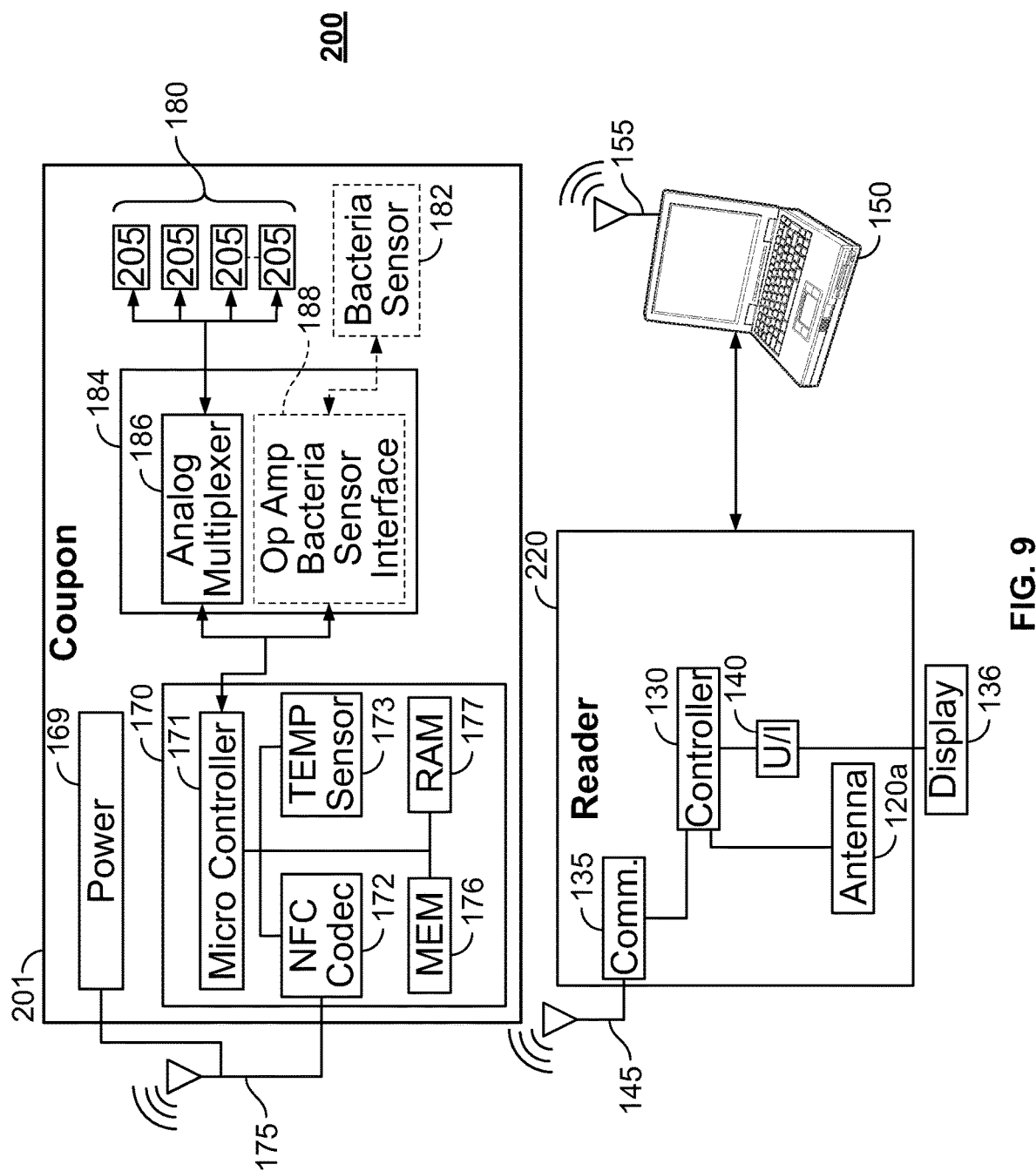
FIG. 9 is a functional diagram of a WMAS according to one embodiment.

Referring now to FIG. 9, a functional illustration of a WMAS 200 is shown according to one embodiment. In this embodiment, wireless communication between the reader and coupon can be accomplished using a digital circuitry schema. For the sake of consistency throughout this disclosure, in the description that follows, reference to coupon, moisture sensor(s), reader and computing device refer to the WMAS components in a general sense as previously described, notwithstanding the differences of the analog and digital components of the reader and coupon in each respective section of this disclosure.

In this embodiment, the coupon 201 and reader 220 of WMAS 200 are configured with circuitry and modules for supporting digital acquisition of moisture sensor readings and digital transmission of moisture readings and associated data from the coupon 201 to the reader 220. Like the analog WMAS 100 counterparts, some circuit components, including, but not limited to the moisture sensors 205 can be disposed on coupon 201 by a selected circuit-printing technique. For example, copper etching, a technique commonly used in the production of RFID tags can be used. To facilitate rapid and inexpensive circuit deposition, however, the technique of inkjet circuit printing can be used. In this preferred technique, the electronic circuitry of coupon 201 can be printed directly on the coupon substrate using, preferably, a bio-compatible ink such as a silver nanoparticle ink. Other integrated circuit elements, such as control module 170 described below can be adhered to, or integrated into the coupon substrate by known methods.

In this embodiment, coupon 201 includes a control module 170 which, in this embodiment can be a fully-operational system-on-a-chip (SoC) configured for near-field communications (NFC) between the coupon 201 and reader 220. The control module 170 can function, in part, as a transceiver, similar to transceiver 125 discussed with respect to FIG. 2. In general, similar to the analog counterpart, the circuitry of coupon 201 can be powered by energy transmitted from an antenna 120a of the reader 220. For example, the coupon 201 can include a power module 169 configured to receive RF energy which can be in circuit communication with other components of the coupon 201 requiring energy to function. The coupon 201 can thusly be energized to engender one or more data measurements to be taken, such as one or more moisture level readings as described in greater detail below. Once the measurements are complete, the measurement data can be transmitted by coupon 201 to reader 220. For example, the control module 170 can include a near-field communications module configured to transmit data from the coupon 201 to the reader 220. In one embodiment, the reader 220 can supply energy to the control module 170 through electromagnetic coupling and the digital response from the coupon 201 can be transmitted through backscatter to the reader 220. In a preferred embodiment, this form of energy harvesting and data transfer is accomplished through electromagnetic induction between the reader 220 and the coupon 201. In this embodiment, reader 220 can be configured in a similar fashion as a radio frequency identification (RFID) scanner.

In this embodiment, control module 170 includes an ISO15693 radio-frequency interface with coupon antenna 175. In this embodiment, antenna 175 is a printed circuit disposed on a top side 102a of the coupon substrate 102 that is configured to harness energy transmitted by reader antenna 120a necessary to power circuitry, modules and any other components of the coupon 201 through inductive coupling. Accordingly, in this embodiment, the antenna 175 circuit is in electronic communication with at least the control module 170 and the power module 169. As such, coupon 201 does not necessarily require an on-board, stored power source such as a battery or wired electrical connection to carry out the functions of the coupon 201 as described herein, although such a configuration could be used in an alternative embodiment. The wireless configuration described herein advantageously provides the wearer with the same type of unrestricted mobility as if he were wearing a regular wound dressing.

In this embodiment, control module 170 can be a stand-alone near-field communications sensor transponder such as the RF430FRL152H sensor transponder by Texas Instruments, Dallas, Tex., USA. In such an embodiment, the sensor transponder can be in circuit communication with one or more moisture sensors 205, temperature sensor 173, and bacteria sensor 182 of the coupon 201.

In general, the control module 170 can store and analyze moisture sensor data to interpret results, e.g., moisture map data (as described in greater detail below) can be tabulated and transmitted to the reader to be displayed for clinical interpretation. Alternatively, or in combination, moisture sensor data can be stored and analyzed in the controller 130 of the reader 220. In one approach, a shared processing routine can utilize both controllers 171, 130; e.g., the coupon processor 170 can perform moisture sensor data preprocessing, filtering and formatting and the reader controller 130 can perform display and post measurement signal processing, including linearizing moisture sensor data.

In one embodiment, control module 170 can include an integrated circuit microcontroller 171. Microcontroller 171 can be selected from available commercial sources according to preference to address desired performance characteristics, power consumption or other aspects of coupon 101 functionality. One exemplary, non-limiting microcontroller that can be used is the MSP430 ultra-low power, 16-bit microcontroller provided by Texas Instruments, Inc., Dallas, Tex., USA. In this embodiment, microcontroller 171 is in electronic communication with the modules, sub-modules and sensor circuitry of the coupon 201, and is programmable to collect measurements, e.g., moisture and bacteria sensor measurements, alone or concurrently, as described herein. Microcontroller 171 is also in signal communication with antenna 175, enabling sensor measurements to be transmitted to reader 220.

In this embodiment, control module 170 further includes a conversion sub-module 172 to convert digital data, e.g., moisture sensor data as described herein, to wireless signals according to a NFC standard codec.

In this embodiment, control module 170 further includes first (176) and second (177) memory modules that can be used, e.g., for storing executable software instructions for carrying out various data-collecting functions as described herein, such as collecting sensor measurements, and storing data associated with those measurements. In one example, the first memory module can be a 2 KB non-volatile ferroelectric memory, and the second memory module can be an 8 KB read-only memory (ROM).

In this embodiment, the control module 170 can optionally include an electronic temperature sensor. The temperature sensor can be used, e.g., to linearize moisture sensor data. In embodiments that include a temperature sensor, temperature measurements can be recorded and transmitted along with moisture sensor measurements. In this and other embodiments, temperature and moisture sensor data can be cooperatively used to correlate with bacteria sensor 182 data to assess the impact of bacteria on moisture sensor readings and to model bacterial activity.

In this embodiment, coupon 201 further includes an analog front-end component 184. In this embodiment, the analog front-end component includes a multiplexer 186 that is configured to allow controller 170 to excite and gather moisture measurements from one or more moisture sensor circuits 205 of the coupon. In this and other embodiments, coupon 201 can include as many moisture sensor circuits as desired. For example, in this embodiment, moisture sensor array 180 includes a plurality of individual moisture sensors 205 which are each configured to operate as electrochemical transducers to measure wound moisture. In general, controller 170 can be configured to excite and gather data for all moisture sensors 205 concurrently, individually or according to a predetermined pattern.

Figure 10:
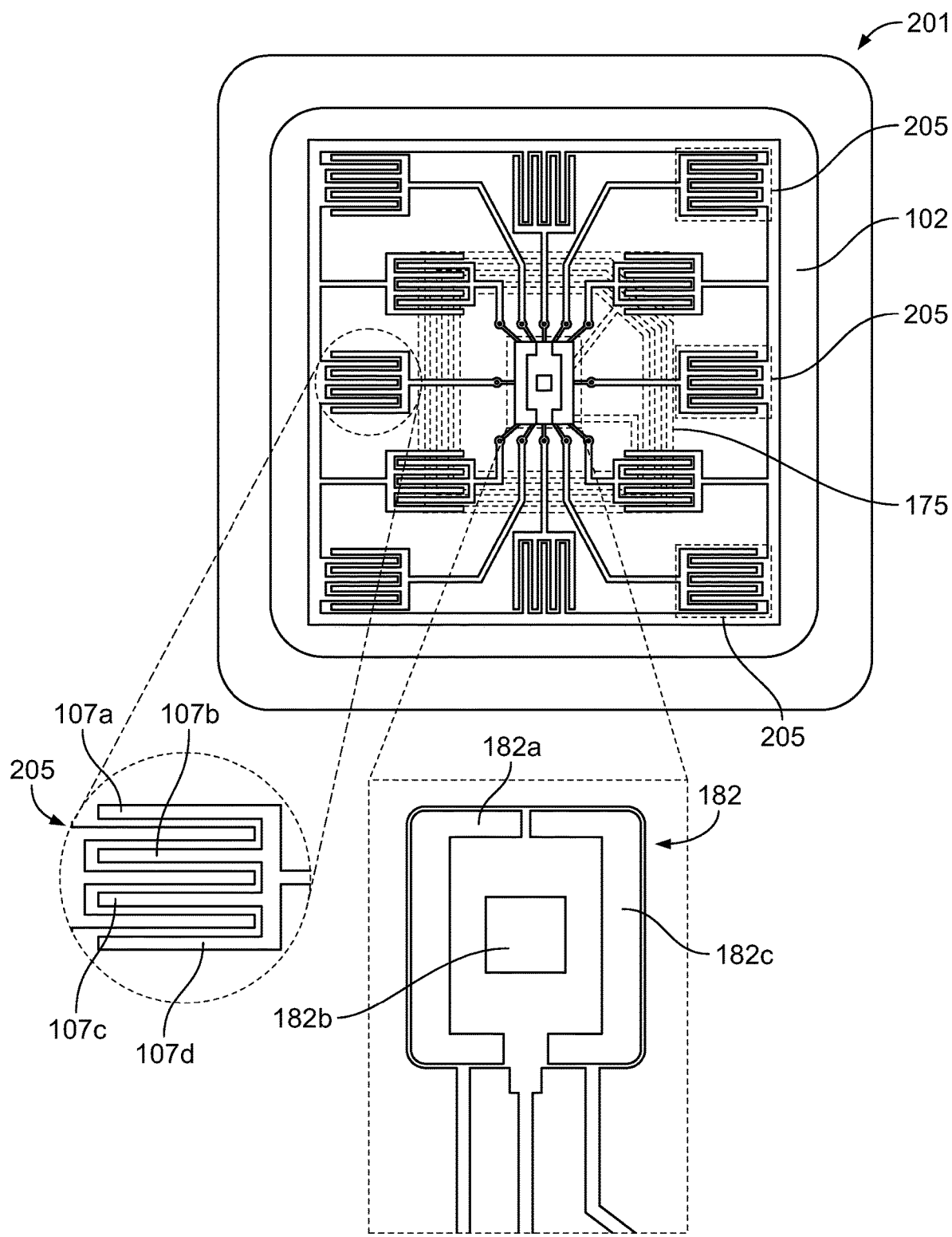
FIG. 10 illustrates a moisture sensor circuit according to one embodiment.

Referring to FIG. 10, digital acquisition of moisture sensor 205 data in this embodiment differs from the previously-described analog counterpart mainly in that each sensor 205 is configured as a stand-alone electrochemical transducer that is in signal communication with microcontroller 171 via analog multiplexer 186. In this embodiment, like the analog counterpart, each sensor 205 includes interdigitated electrodes 107a-d. However, direct multiplexing obviates the resistor R and inductor L sensor circuit elements used in the analog counterpart (see, e.g., FIG. 7). Thus, in the digital schema presently discussed, capacitance is used to model an impedance change which is correlatable to a moisture level across sensor electrodes 107a-d. In the analog counterpart, the inductor L is used to model the transmitter and receiver antenna coupling, which through the waveform analysis discussed previously, can provide correlation to moisture levels across electrodes 107a-d (FIG. 7).

In this embodiment, the analog front-end component 184 further includes an operational amplifier 188 as an interface to an electrochemical bacteria sensor 182. Bacteria sensor 182 can be used, e.g., to detect and quantify contamination of moisture sensors 205 from exudate due to proliferation of bacteria and onset of infection. In this embodiment, bacteria sensor 182 is centrally disposed on bottom side 102a of the coupon substrate and includes a Ag/AgCl reference electrode 182a, and a carbon-based working (182b) and counter (182c) electrode.

In one approach, the influence of exudate on sensor 205 impedance can be quantified and corrected for by, e.g., modeling bacterial contamination. Without wishing to be bound by theory, it is believed that impedance 'interference' due to bacterial contamination is caused by two primary sources: the first being microbial metabolism, which alters the conductivity of the medium; the second is electrode interfacial impedance, results when the presence of bacteria changes the surface properties of the electrodes, which can affect the capacitance of the electrode/electrolyte interface. Thus, growth of microorganisms such as bacteria usually results in an increase in both conductance and capacitance, causing a decrease in impedance. In this embodiment, temperature sensor 173 can provide an additional modeling and measuring parameter to account for the temperature effect on electrode capacitance, metabolic behavior of bacteria, and evaporation Referring back to FIG. 9, in this embodiment, wireless reader 220 includes a microcontroller 130 in electronic signal communication with antenna 120a, a communications module 135 and a user interface 140 which itself is in signal communication with an external display 136. In a preferred embodiment, display 136 is a touch-screen display device that allows a user to input information, control functionality of the reader, activate moisture sensor scans, etc. However, reader 220 can optionally include buttons, keyboards or other user-controllable input devices which are not shown in FIG. 9 for the sake of figure clarity.

In this embodiment, controller 130 is configured to emit a controllable activation signal, e.g., an RF signal from antenna 120a that provides sufficient energy to power energy-necessary components of coupon 201, e.g., controller 170, and to allow moisture sensor 205 measurements to be taken. In a preferred embodiment, antenna 175 of coupon 201 is configured to receive the activation signal from reader 220 with minimal energy loss. In this embodiment, each of the one or more moisture sensors 205 can be used to collect a moisture sensor reading which is then transmitted back to reader 220 via antenna 175.

In a preferred embodiment, microcontroller 130 includes at least a processor, a memory, and electronic data and command storage capabilities, e.g., RAM or ROM for electronically storing instructions for activating the one or more moisture sensors 205 and receiving moisture sensor readings therefrom, preferably analyzing those data, and transmitting the moisture sensor reading results to the computing device 150.

In this embodiment, microcontroller 130 is in signal communication, e.g., through the use of an input/output port, with user interface 140. User interface 140 can include, without limitation, a screen for displaying information relating to the acquisition of moisture sensor data, moisture analysis results and related data, historical data, and other information. In a preferred embodiment, user interface 140 can include a touch-sensitive display screen 136 that provides the capability of entering user input, e.g., patient-identifying information, general system settings (date, time, interrogation frequency, etc.), computer network settings providing the capability of transmitting data from the WMAS 100 to a computer network, e.g., through the use of wired or wireless signal communications, activation buttons configured to initiate a wound moisture assessment, and other functions.

In this embodiment, microcontroller 130 is in signal communication with a communications module 135 that is configured to transmit moisture sensor readings to computing device 150. The communications module 135 can be configured to provide bi-directional, electronic communication between the WMAS 100 and the remote computing device 150 by any preferred wired or wireless communications protocol or standard, such as WIFI, BLUETOOTH, IR, etc. In this embodiment, for reliable signal transmission, the communications module 135 communicates with remote computing device 150 using wireless antennas 145 and 155, respectively. In a preferred embodiment, the wireless reader 220 can be in the form of an RFID scanner gun which collects moisture sensor readings and transmits those data to computing device 150 so that they may be processed into a user-friendly format such as a wound moisture map.

In this embodiment, coupon 201 can be powered through electromagnetic induction with reader 220 RF emission at, e.g., NFC frequencies of 13.56 MHz or other chosen frequencies. The reader 220 can use NFC standard techniques to power and communicate with the coupon; in such a case, the reader 220 can be implemented with a smartphone or other standard NFC device.

In this and other embodiments, reader 220 can be configured to transmit moisture sensor measurements from coupon 101 to computing device 150. Communication between the reader 220 and computing device 150 can be accomplished by any preferred wired or wireless communications protocol or standard, such as Ethernet, WIFI, BLUETOOTH, IR, etc. In general, moisture sensor measurements need not be directly between the reader 220 and the computing device 150. For example, reader 220 can be in signal communication with a wireless router, access point or other communications hub which directs the measurement traffic to computing device 150 via a computer network, such as a LAN or the Internet, by known methods as disclosed above.

In this and other embodiments, computing device 150 can be configured to display information relating to the acquisition of moisture sensor data, moisture analysis results and related data, historical data, and other information via a software package. In a preferred embodiment, reader 220 can be configured to allow the user to enter information, such as the user's name, a patient ID, location, bed number, wound location, date, time, wound interrogation frequency or other data through a programmable user interface. The user-supplied information can be transmitted along with moisture sensor measurements from the reader 220 to the computing device 150 and, for example, compiled to form a data set. In one embodiment, the user interface can include a touch-sensitive display screen that provides the capability of entering user input, computer network settings providing the capability of transmitting data from the reader 220 to a computer network, e.g., through the use of wired or wireless signal communications, activation buttons configured to initiate a wound moisture assessment, and other functions.

Moisture Mapping

Figure 11:
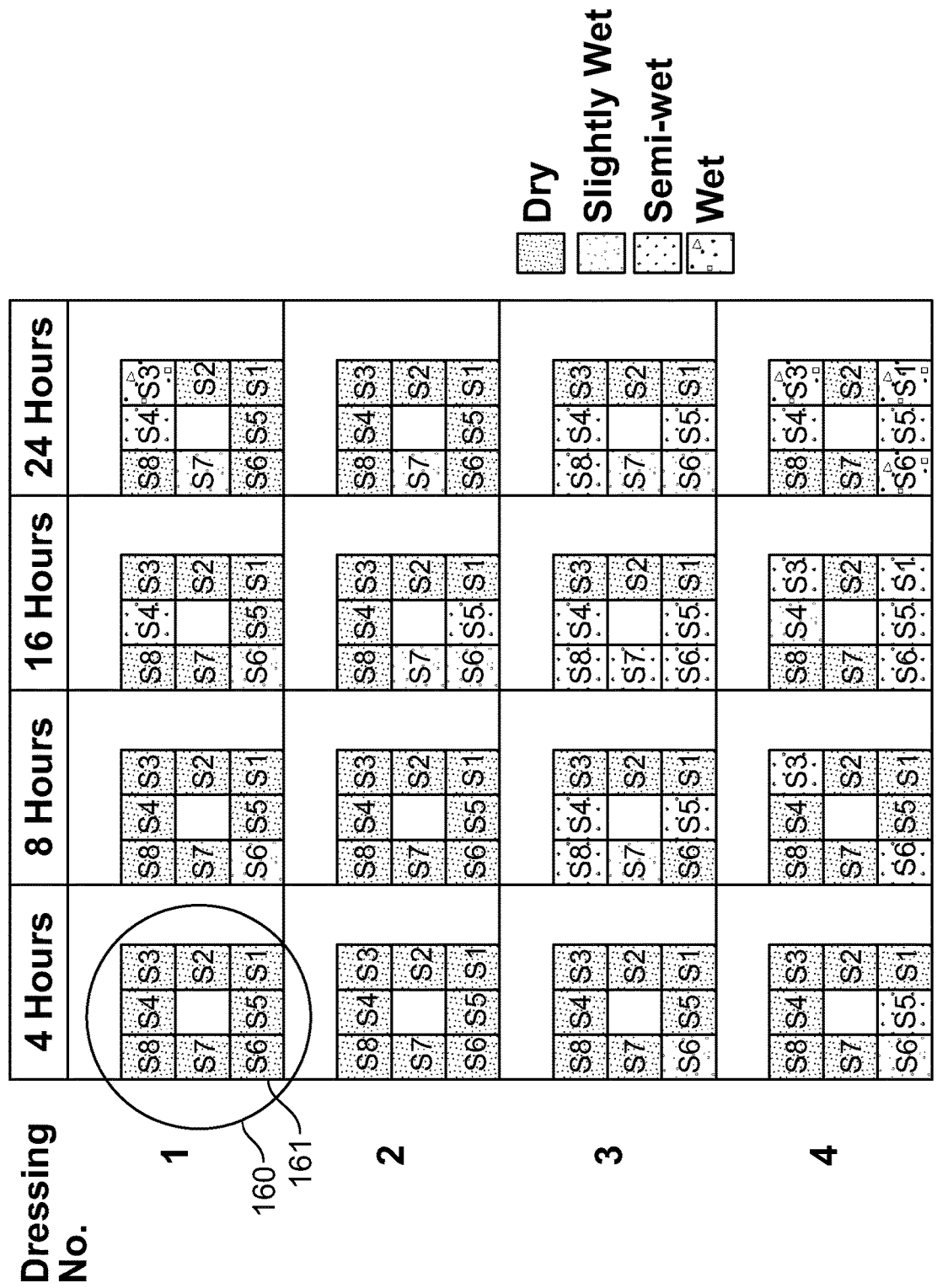
FIG. 11 illustrates a series of wound moisture maps according to one embodiment.

Referring now to FIG. 11, in general, WMAS 100 can be utilized to create a wound moisture map 160 of a wound. A moisture map of the type described herein can reflect moisture sensor data whether obtained by the analog or digital schemas described herein. A wound moisture map 160 can be a graphical representation of the moisture levels of a wound, as measured in different areas of the wound by the sensors 105/205 of coupon 101/201. In general, a wound moisture map 160 can help to ascertain wound moisture imbalance and, in a preferred approach, such a map can be collected at selected intervals over a time period to monitor and manage acute and chronic wounds.

For example, FIG. 11 shows a plurality of moisture maps 160 for first, second, third and fourth dressings taken at 4, 8, 16 and 24-hour time intervals. In this illustration, each labeled square S1-S8 represents a moisture level measured by a corresponding moisture sensor S1-S8 of coupon 101 illustrated in FIG. 7. For example, square 161 graphically depicts the measured moisture level of the wound corresponding to sensor S6 of coupon 101.

In this and other embodiments, moisture map 160 can be graphically displayed using a legend to indicate a qualitative or quantitative moisture sensor reading. In the examples shown in FIG. 11, each moisture map 160 graphically depicts moisture sensor readings according to a "Dry," "Slightly Wet," "Semi-Wet" and "Wet" legend scale. The legend scale can be selected according to preference to correlate to a quantitative moisture level as measured by the moisture sensors 105. Alternatively, moisture map 160 could display quantitative data that show actual moisture levels as measured by each sensor 105/205, which can be expressed in any desired measurement unit.

In one approach, a coupon 101/201 provides the ability to dispose one or more moisture sensors at the perimeter of a wound where moisture sensing can be critical to: 1) understand where undermining (e.g., deep tissue damage under the wound margin) is occurring; 2) interpreting where maceration exists or where the locations where the wound perimeter is too dry, which can limit blood flow and irrigation of the wound bed; 3) ascertaining the true border of the wound; 4) ascertaining where new tissue could be forming or where granulation of tissue (epithelialization) is occurring; and 5) ascertaining where, and if infection is present.

FIG. 11 shows an array of moisture maps 160, each for a first through fourth dressing. For example, the top-left moisture map 160 corresponds to a measurement of a first coupon 101 (which may, e.g., be integrated into a wound dressing) at the 4-hour interval, and indicates that the respective portions of a wound adjacent to sensors S1-S8 are dry. At the 8-hour interval, the reading for moisture sensor S6 indicates a slightly wet environment; at the 16-hour interval, the reading for moisture sensor S6 continues to indicate a slightly wet environment and moisture sensor S4 indicates a semi-wet environment; at the 24-hour interval, moisture sensor S6 indicates a dry environment while sensor S7 indicates a slightly wet environment, and sensors S4 and S3 indicate semi-wet and wet environments, respectively.

The exemplary data shown in FIG. 11 illustrate how coupon 101/201 having an array of moisture sensors 105/205 can be used to monitor physiological changes in a wound bed over time; accordingly, these data can be used in caring for the wound or providing an alert that wound healing is occurring or not. The beneficial effects of a moist versus dry wound environment include: prevention of tissue dehydration and cell death, accelerated angiogenesis, increased breakdown of dad tissue and fibrin, e.g., pericapillary fibrin cuffs, and potentiating the interaction of growth factors with their target cells. In this and other embodiments, the extrapolation of moisture sensor data (explained in greater detail below) or the sensors themselves can be calibrated according to preference so that the relative terms "wet" "slightly wet" "semi-wet" and "wet" can reflect different degrees of wound moisture or exudate in a moisture map. In a complex wound such as a pressure ulcer being treated with a vacuum-assisted closure (VAC) device, for example, points of desiccation and alternatively areas of pooling of exudate may exist. The WMAS 100/200 can identify these areas and allow caregivers or the patient himself to modify their care to optimize the moisture of the wound for proper healing.

Figure 12:
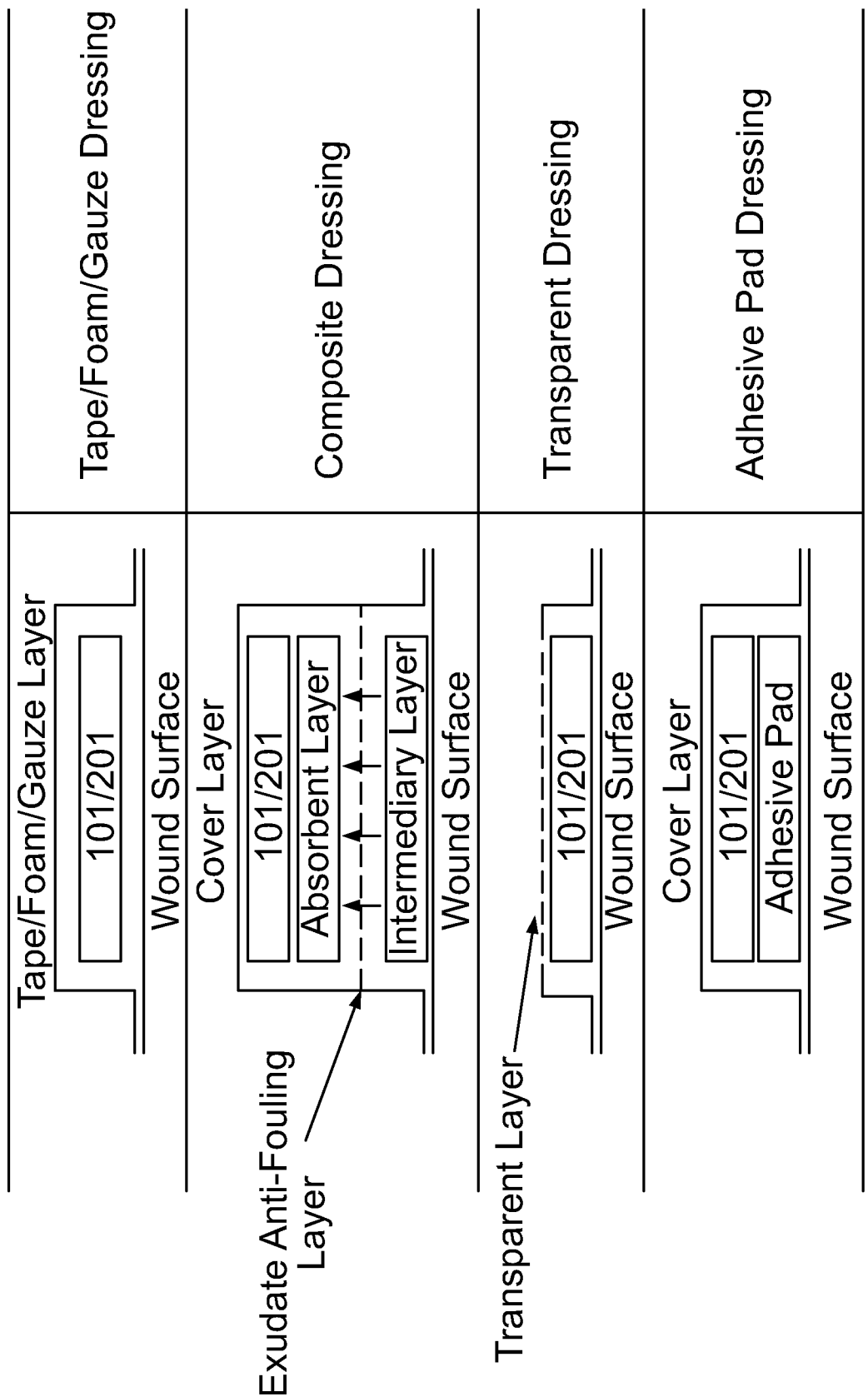
FIG. 12 illustrates a WMAS coupon integrated into different types of wound dressings.

Referring now to FIG. 12, coupon 101/201 can be integrated into a protective wound dressing or bandage of any kind. For example, coupon 101/201 can be disposed on one side of a protective dressing and configured such that it can be applied directly to a wound, such as, but not limited to a venous, arterial, pressure or diabetic wound. In an alternative embodiment, the coupon 101/201 can be integrated into a protective dressing such that it is disposed between top and bottom layers of the dressing. In such an approach, the dressing can provide at least one layer of protective material between the wound bed and the coupon 101/201.

Some exemplary, non-limiting types of dressings that coupon 101/201 can be integrated with include: tape and foam dressings, where coupon 101/201 can be disposed between the foam layer and the cover layer; transparent films, where coupon 101/201 can be printed directly on the film window; gauze, where coupon 101/201 can be embedded therein or thereon; composites, where coupon 101/201 can be embedded in intermediary layer or printed on the cover layer; and alginate, where coupon 101/201 can be disposed therein or on a secondary dressing.

In one embodiment, an exudate anti-fouling layer can be integrated into the dressings to reduce the deleterious effects of exudate adherence and acidity build-up between the wound and the dressing. This is illustrated in FIG. 12 by the dashed line between the intermediary layer and the absorbent layer. In such an embodiment, the anti-fouling layer can be perforated to promote exudate diffusion therethrough; and, in one embodiment, the holes of the perforated layer can contain exudate filter material to minimize exudate contamination of the coupon 101/201 components. Other applicable dressings will be evident to those skilled in the art.

A number of illustrative embodiments have been described. Nevertheless, it will be understood that various modifications may be made without departing from the spirit and scope of the various embodiments presented herein. For example, other moisture sensor configurations and layouts can be substituted for those described herein. At least one multi-element sensor array is described in U.S. patent application Ser. No. 14/690,324 filed on Apr. 17, 2015 by J. N. Schoess et al., which is incorporated by reference in its entirety herein. Accordingly, other embodiments are within the scope of the following claims.

What is claimed is:

1. A coupon for wireless communication with a transceiver, comprising:
    a flexible substrate having a top surface and a bottom surface;
    a radio-frequency antenna circuit disposed on said top surface of said flexible substrate;
    at least one electrochemical moisture sensor circuit disposed on said bottom surface of said flexible substrate that is configured to determine a moisture level of a plurality of different moisture levels of the flexible substrate, wherein more than one moisture level of the plurality of different moisture levels correspond to a qualitative moisture level that indicates a degree of wetness of the flexible coupon, wherein said at least one electrochemical moisture sensor circuit comprises an array of electrochemical moisture sensor circuits;
    a multiplexer in electronic communication with said array of electrochemical moisture sensor circuits; and
    an adhesive having a top surface and a bottom surface, wherein said bottom surface of said adhesive is configured to be attached to skin of a user and wherein said at least one electrochemical moisture sensor is arranged between said adhesive and said flexible substrate.

2. The coupon of claim 1, further comprising a near-field communications module disposed on said top surface of said flexible substrate that is in electronic communication with said radio-frequency antenna circuit.

3. The coupon of claim 2, wherein said near-field communications module comprises:
    a microcontroller in signal communication with said radio-frequency antenna circuit and said at least one electrochemical moisture sensor circuit; and
    a memory for storing executable logic functions for measuring a moisture value of an environment proximal to said at least one electrochemical moisture sensor circuit.

4. The coupon of claim 3, wherein said near-field communications module further comprises:

a signal converter capable of converting analog signals to digital signals and vice-versa; and an optional temperature sensor.

5. The coupon of claim 2, further comprising a bacteria sensor disposed on said bottom surface of said flexible substrate that is in signal communication with said near-field communications module.

6. The coupon of claim 2, wherein said near-field communications module is configured to receive operational power from an external radio-frequency source that is received by said radio-frequency antenna circuit.

7. A system for wirelessly obtaining a moisture measurement, comprising:
   a wireless reader comprising a transceiver configured to emit and receive radio frequency signals; and
   a coupon comprising:
      a flexible substrate having a top surface and a bottom surface;
      at least one electrochemical moisture sensor circuit disposed on said bottom surface of said flexible substrate that is configured to determine a moisture level of a plurality of different moisture levels of the flexible substrate, wherein more than one moisture level of the plurality of different moisture levels correspond to a qualitative moisture level that indicates a degree of wetness of the flexible coupon, wherein said at least one electrochemical moisture sensor circuit comprises an array of electrochemical moisture sensor circuits;
      an antenna circuit disposed on said top surface of said flexible substrate configured to at least receive said radio frequency signals from said transceiver;
      a microcontroller in electronic communication with said antenna circuit and said at least one electrochemical moisture sensor circuit;
      a multiplexer in electronic communication with said microcontroller and said array electrochemical moisture sensor circuits; and
      an adhesive having a top surface and a bottom surface, wherein said bottom surface of said adhesive is configured to be attached to skin of a user and wherein said at least one electrochemical moisture sensor is arranged between said adhesive and said flexible substrate.

8. The system of claim 7, further comprising a bacteria sensor circuit disposed on said bottom surface of said flexible substrate and configured to be in electronic communication with said microcontroller.

9. The system of claim 7, wherein said microcontroller is configured to obtain said moisture level from said at least one electrochemical moisture sensor circuit.

10. The system of claim 9, wherein said microcontroller is configured to wirelessly transmit said moisture measurement to said wireless reader via said antenna circuit.

11. The system of claim 7, wherein said moisture level is determined by obtaining a capacitance value of said at least one electrochemical moisture sensor circuit.

12. The system of claim 7, wherein said coupon is disposed on, or within a wound dressing or bandage.

13. The system of claim 7, wherein said microcontroller is configured to be powered by said radio frequency signal emitted by said transceiver of said wireless reader.

14. The system of claim 7, wherein said multiplexer is configured to obtain a capacitance value of each of said electrochemical moisture sensor circuits.

15. A system for generating a wound moisture map, comprising:
   a flexible coupon having a top surface and a bottom surface, wherein said bottom surface is configured to be applied at least in part to a wound or ulcer;
   an antenna circuit and a microcontroller disposed on said top surface of said coupon, wherein said microcontroller is in electronic communication with said antenna circuit; and
   a plurality of electrochemical moisture sensor circuits disposed on said bottom surface of said coupon;
   a multiplexer in electronic communication with said microcontroller and said plurality electrochemical moisture sensor circuits;
   wherein each electrochemical moisture sensor circuit of said plurality of electrochemical moisture sensor circuits is in electronic communication with said microcontroller and wherein each electrochemical moisture sensor circuit of said plurality of electrochemical moisture sensor circuits is configured to determine a moisture level of a plurality of different moisture levels for a different region of the flexible coupon, wherein more than one moisture level of the plurality of different moisture levels correspond to a qualitative moisture level that indicates a degree of wetness of the flexible coupon; and
   wherein said antenna circuit is adapted to send and receive radio frequency signals to and from a remote radio frequency transceiver, respectively.

16. The system of claim 15, further comprising an electrochemical bacteria sensor disposed on said bottom surface of said coupon that is in electronic communication with said microcontroller.

17. The system of claim 15, further comprising an electronic temperature sensor disposed on said bottom surface that is in electronic communication with said microcontroller.

18. The system of claim 15, wherein said microcontroller is configured to:
   receive query signals from said transceiver via said antenna;
   query said plurality of electrochemical moisture sensor circuits in a selective or group-wide modality for one or more wound moisture measurements; and
   transmit said moisture measurements to said transceiver via said antenna.

19. The system of claim 15, wherein each electrochemical moisture sensor circuit of said plurality of electrochemical moisture sensor circuits comprises an array of interdigitated electrodes.

* * * * *

UNITED STATES PATENT AND TRADEMARK OFFICE
CERTIFICATE OF CORRECTION

PATENT NO. : 11,141,100 B2
APPLICATION NO. : 15/390439
DATED : October 12, 2021
INVENTOR(S) : Schoess et al.

It is certified that error appears in the above-identified patent and that said Letters Patent is hereby corrected as shown below:

In the Specification

In Column 1, Line 40, delete "billon" and insert -- billion --, therefor.

In Column 14, Line 45, delete "102a" and insert -- 102b --, therefor.

Signed and Sealed this
Twenty-first Day of June, 2022

*Katherine Kelly Vidal*
Katherine Kelly Vidal
*Director of the United States Patent and Trademark Office*